US00PP08856P

United States Patent [19]

Olesen et al.

[11] Patent Number: Plant 8,856

[45] Date of Patent: Aug. 9, 1994

[54] MINIATURE ROSE PLANT NAMED 'POULVERT'

[75] Inventors: Mogens N. Olesen; Pernille Olesen, both of Fredensborg, Denmark

[73] Assignee: Bear Creek Gardens, Inc., Medford, Oreg.

[21] Appl. No.: 96,698

[22] Filed: Jul. 23, 1993

[51] Int. Cl.[5] ..... A01H 5/00

[52] U.S. Cl. ..... Plt./8.2

[58] Field of Search ..... Plt. 8.2

[56] References Cited

U.S. PATENT DOCUMENTS

P.P. 1,957 8/1957 Moore ..... PLT/8.2

*Primary Examiner*—Howard J. Locker

*Attorney, Agent, or Firm*—Klarquist Sparkman Campbell Leigh & Whinston

[57] ABSTRACT

A miniature class rose plant with yellow flower color and many prickles on the flower stems.

1 Drawing Sheet

The present invention relates to a new and distinct variety of rose plant of the miniature class which was originated by us by crossing two unnamed seedlings.

The primary objective of this breeding was to produce a new miniature rose variety that can be potforced and grown from cuttings. The objective was substantially achieved along with other desirable improvements.

Asexual reproduction of this new variety by softwood cuttings, as performed at Somis, Calif. and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where oridinary dictionary significance of color is indicated.

Parentage:

*Seed parent.*—An unnamed seedling.

*Pollen parent.*—An unnamed seedling.

Classification:

*Botanical.*—Rosa hybrida.

*Commercial.*—Miniature.

FLOWER

Observations made from specimens grown in a greenhouse environment at the premises of Poulsen Roser ApS, Fredensborg, Denmark, in 1990.

Blooming habit: Continuous.

Bud:

*Size.*—1.5 cm long when the petals start to unfurl.

*Form.*—Long, pointed ovoid.

*Color.*—When sepals first divide, bud color is Yellow Group 5C. When half blown, the upper and lower sides of the petals are Yellow Group 5C.

*Sepals.*—Color: Green. Surface texture: Covered in fine hairs. There are three lightly appendaged sepals. There are two unappendaged sepals with smooth edges.

*Receptacle.*—Color: Green Group 138B. Shape: Pitcher shaped. Size: Small. Surface: Smooth.

*Peduncle.*—Length: Long, for a pot rose. Surface: Prickly. Color: Light green. Strength: Stiff, erect.

Bloom:

*Size.*—Small. Average open size is 4 cm in diameter.

*Borne.*—Several together, in pyramidal clusters averaging 3 or 4 flowers.

*Stems.*—Medium (average 15 cm long), strong.

*Form.*—When first open: Cupped. Permanence: Flattens, outer petal edges slightly curl.

*Petalage.*—Number of petals under normal conditions: 30 to 40.

*Color.*—The upper and reverse sides of the petals are Yellow Group 5C. The bases of the petals are Yellow Group 5C. The major color on the upper side is Yellow Group 5C.

*Variegations.*—None.

*Discoloration.*—No change in the general tonality at the end of the first day or at the of the third day.

*Fragrance.*—Slight.

Petals:

*Texture.*—Thin.

*Shape.*—Round.

*Form.*—Tips slightly recurved, edges moderately quilled.

*Arrangement.*—Informal, with few petaloids in the center.

*Persistence.*—Drop off cleanly.

*Lastingness.*—On the plant: Fair (7 to 10 days). As a cut flower: Fair (7 days).

Reproductive parts:

*Anthers.*—Size: Large. Quantity: Many (for a miniature rose). Color: White, yellow. Arrangement: Regular around styles.

*Filaments.*—Color: Yellow.

*Pollen.*—Color; Gold Yellow.

Styles.—Color: White to light yellow.

*Stigmas.*—Color: White.

Form: Bush.

Growth: Dwarf, upright.

Foliage: Number of leaflets on normal mid-stem leaves: 5.

*Size.*—Small.

*Quantity.*—Normal.

*Color.*—New foliage: RHS Green Group 139C Old foliage; Green Group 137B.

Leaflets:

*Shape.*—Oval pointed.

*Texture.*—Upper side: Smooth.

*Edge.*—Serrated.

*Serration.*—Single, small.

*Petiole rachis.*—Color: Green.

*Petiole underside.*—Smooth.

*Stipules.*—Medium, serrated.

*Disease resistance.*—Resistant to mildew under normal growing conditions in Denmark and at Somis, Calif.

Wood:

*New wood.*—Color: Light green. Bark: Smooth.

*Old wood.*—Color: Green. Bark: Smooth.

Prickles:

*Quantity*—On main canes from base: Ordinary. On laterals from main canes: Few.

*Form.*—Straight.

*Color when young.*—Red, translucent.

Small Prickles:

*Quantity.*—On main stalks: Few. On peduncle: Many.

*Color*—Light, yellowish green, translucent.

I claim:

1. A new and distinct variety of rose plant of the miniatue class, substantially as herein shown and described, characterized particularly as to novelty by the unique combinatin of its yellow flower color and many prickles on the flower stems.

* * * * *

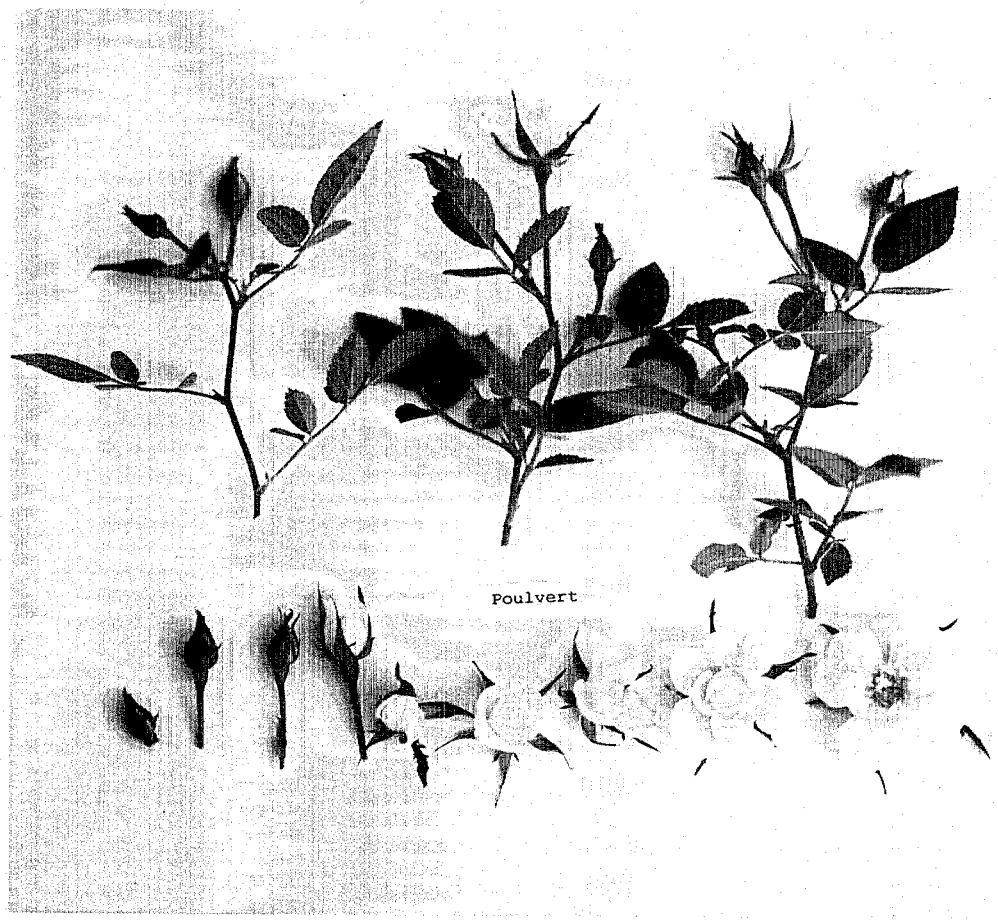
Poulvert